United States Patent
Zhou et al.

(10) Patent No.: US 10,010,308 B2
(45) Date of Patent: Jul. 3, 2018

(54) SYSTEM AND METHOD FOR CT-GUIDED NEEDLE BIOPSY

(75) Inventors: Yu Zhou, White Plains, NY (US); Kaarvannan Thiruvalluvan, Stony Brook, NY (US); Lukasz Krzeminski, Brooklyn, NY (US); William H. Moore, Setauket, NY (US); Zhigang Xu, Lake Grove, NY (US); Zhengrong Liang, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 979 days.

(21) Appl. No.: 14/232,979

(22) PCT Filed: Jul. 20, 2012

(86) PCT No.: PCT/US2012/047585
§ 371 (c)(1),
(2), (4) Date: Oct. 6, 2014

(87) PCT Pub. No.: WO2013/013142
PCT Pub. Date: Jan. 24, 2013

(65) Prior Publication Data
US 2015/0073259 A1 Mar. 12, 2015

Related U.S. Application Data

(60) Provisional application No. 61/510,195, filed on Jul. 21, 2011.

(51) Int. Cl.
*A61B 6/03* (2006.01)
*A61B 10/04* (2006.01)
(Continued)

(52) U.S. Cl.
CPC .............. *A61B 10/04* (2013.01); *A61B 6/032* (2013.01); *A61B 6/486* (2013.01); *A61B 6/5217* (2013.01);
(Continued)

(58) Field of Classification Search
CPC ................ A61B 10/0233; A61B 10/04; A61B 2010/045; A61B 2034/2057;
(Continued)

(56) References Cited

U.S. PATENT DOCUMENTS

| 6,546,279 | B1 | 4/2003 | Bova et al. |
| 2006/0052693 | A1 | 3/2006 | Tynes et al. |
| 2008/0287827 | A1* | 11/2008 | Sarkar .................... A61B 8/587 600/567 |

FOREIGN PATENT DOCUMENTS

| RU | 2243002 C2 | 12/2004 |
| RU | 2008143211 A | 5/2010 |

OTHER PUBLICATIONS

International Search Report dated Nov. 1, 2012 issued in PCT/US2012/047585.

* cited by examiner

*Primary Examiner* — Ruth S Smith
(74) *Attorney, Agent, or Firm* — Scully, Scott, Murphy & Presser, P.C.

(57) ABSTRACT

An image-guided system and method for performing needle biopsy on a moving lung nodule of a body is provided. CT images of the lung nodule are obtained to generate a motion model, based on which an optimal needle advancing path is determined. The motion of the lung nodule and the motion of a fiducial marker attached to the body are correlated. The motion of the fiducial marker is tracked and monitored by a camera to determine a position of the lung nodule based on the correlation. A time for advancing the needle is deter- (Continued)

mined based on a motion attribute of the reference. The needle is advanced by a robotic needle manipulator at the predetermined time along the path to accomplish the needle placement.

18 Claims, 3 Drawing Sheets

(51) Int. Cl.
    *A61B 10/02*     (2006.01)
    *A61B 6/00*     (2006.01)
    *A61B 8/08*     (2006.01)
    *G01R 33/28*     (2006.01)
    *G01R 33/48*     (2006.01)
    *A61B 34/30*     (2016.01)
    *G06T 7/246*     (2017.01)
    *A61B 34/20*     (2016.01)
    *A61B 90/00*     (2016.01)

(52) U.S. Cl.
    CPC ........ *A61B 8/0841* (2013.01); *A61B 10/0233* (2013.01); *A61B 34/20* (2016.02); *A61B 34/30* (2016.02); *A61B 90/39* (2016.02); *G01R 33/285* (2013.01); *G01R 33/4812* (2013.01); *G01R 33/4814* (2013.01); *G06T 7/251* (2017.01); *A61B 6/506* (2013.01); *A61B 2010/045* (2013.01); *A61B 2034/2057* (2016.02); *A61B 2034/2063* (2016.02); *A61B 2090/374* (2016.02); *A61B 2090/3762* (2016.02); *A61B 2090/3937* (2016.02); *G06T 2207/10081* (2013.01); *G06T 2207/30064* (2013.01)

(58) Field of Classification Search
    CPC ...... A61B 2034/2063; A61B 2090/374; A61B 2090/3762; A61B 2090/3937; A61B 34/20; A61B 34/30; A61B 6/032; A61B 6/486; A61B 6/506; A61B 6/5217; A61B 8/0841; A61B 90/39; G01R 33/285; G01R 33/4812; G01R 33/4814; G06T 2207/10081; G06T 2207/30064; G06T 7/251
    See application file for complete search history.

SYSTEM AND METHOD FOR CT-GUIDED NEEDLE BIOPSY

CROSS-REFERENCE TO RELATED APPLICATIONS

This application claims benefit of U.S. Provisional Application No. 61/510,195 filed on Jul. 21, 2011, the entire contents of which are incorporated herein by reference.

BACKGROUND OF THE DISCLOSURE

The present disclosure relates generally to image-guided tissue sampling and, more particularly, to a system and method for Computed Tomography (CT)-guided needle biopsy for sampling lung nodules with respiratory motion.

Lung cancer is the most common cause of cancer-related death in men world-wide and the second most common cause of cancer-related death in women, resulting in 1.3 million deaths per year. Early diagnosis and detection is critical to reduce morbidity and mortality rates in high-risk individuals who are screened for lung cancer. Lung nodules, the precursor to lung cancer, are often detected by imaging examinations, such as X-ray and CT. However, it is not always possible to tell from these imaging studies whether a lesion is benign or cancerous. To confirm the diagnosis, a needle biopsy is often performed to obtain tissue samples from the suspicious area for microscopic examinations.

CT-guided needle biopsy has become a dominant method of obtaining tissue samples from lung nodules for lung cancer diagnosis and is performed by a specially trained interventional radiologist. The patient will lie on a CT table, and receives a local anesthesia injection to numb the needle path. The suspicious nodule is located through a pre-operative CT scan, and the safest needle path will be planned based on the scan. The patient will be required to stay still and hold his/her breath during the procedure. Using intra-operative CT scans to confirm the positions of the nodule and needle, the clinician inserts the needle through the skin, advance it to the target nodule, and removes tissue samples. CT-guided needle biopsy is minimally invasive, eliminating the added morbidity of open surgery and requiring no general anesthesia. The procedure is generally not painful. The patient quickly recovers able to return home and resumes their usual activities the same day.

Tissue sampling accuracy and patient safety are critical in the CT-guided needle biopsy of lung nodules, and impose serious challenges. Accurate needle placement depends on the clinician's skill and consistency and the patient's compliance. The nodule size and location contribute to the difficulty in needle placement. Although ideally located nodules as small as 4 mm have been successfully biopsied in case reports, as a general rule, lesions ≤8 mm are very difficult to approach and successfully biopsy. The diagnostic accuracy generally decreases with smaller lesions and longer needle paths. Moreover, to implement a rapid, safe and accurate biopsy, it is necessary for the patient to remain still and repeatedly hold his/her breath during needle manipulations. Breath holding can be a significant problem when a lesion is close to the diaphragm because the lung nodule can be displaced up to 20 mm or even higher during a respiratory cycle. Thus, it is highly challenging to perform biopsies in patients who have difficulties in holding their breath, which accounts for about 10%-15% of the entire patient pool. In addition, the procedure duration ranges from 15 minutes to over an hour, depending on CT, cytology availability, nodule accessibility and patient compliance. Inaccurate needle positioning and insufficient patient compliance necessarily increase the number of needle passes and occurrence of complications such as pneumothorax and bleeding. These issues can be overcome by extremely experienced physicians. However, the widespread availability of these physicians is limited.

Image-guided robots have been growing as an important technological advance to assist image-guided percutaneous procedures. Various robotic percutaneous systems have been developed or researched, from general-purpose percutaneous systems to those specialized for neurosurgery, prostate interventions, breast biopsy and therapy, renal access and other similar procedures, under the guidance of different imaging modalities such as CT/fluoroscopy, ultrasound and MR. Generally, the needle path is determined by the clinician based on initial imaging, usually by choosing the target and skin-entry points; the robot moves the needle to a starting position and aligns it to the pre-planned needle path; and the needle is inserted to the desired depth manually or robotically. Automatic feedback control of needle movement has also been proposed, such as the needle movement adjustment based on CT and MR image processing and the more real-time needle trajectory control based on ultrasound image processing, single-plane CT image processing and tracking sensor feedback. Moreover, there is a category of robotic percutaneous systems, which combine the manual adjustment and robotic needle alignment/driving and can be controlled by the clinician using a joystick using real-time image display.

However, the above systems focus on handling generally static organs and lack integrated control schemes for needle placement on moving targets, such as lung nodules with respiratory motion. Thus, known systems cannot obtain high targeting accuracy and short procedure duration with respect to moving targets. Particularly, in the scenario of CT-guided needle biopsy of moving lung nodules, it may result in an increase in the number of needle passes, occurrence of complications and radiation exposure on the patient.

Therefore, there is a need to implement a CT-guided robotic needle biopsy on moving targets, such as lung nodules with respiratory motion, with improved biopsy accuracy and reduced biopsy duration, which does not require arduous patient compliance during the interventional procedure, such as breath holding. Accordingly, in accordance with the present disclosure, the incidence of complications can be reduced, patient safety can be improved, and human intervention can be minimized.

BRIEF DESCRIPTION OF THE DISCLOSURE

As described herein, the exemplary embodiments of the current disclosure overcome one or more of the above or other disadvantages known in the art.

One exemplary aspect of the present disclosure relates to a method of performing needle biopsy on a moving target in a body. The method includes acquiring a plurality of images of the moving target, within a predetermined timeframe; generating a motion model of the moving target based on the plurality of images; generating a needle advancing path for a biopsy needle, based on the motion model of the moving target; establishing a correlation between at least one motion attribute of the moving target and at least one motion attribute of a reference; tracking the motion of the reference to determine a value of the at least one motion attribute of the reference; determining a time for advancing the biopsy needle based on the value of the at least one motion attribute of the moving target; determining a value of the at least one motion attribute of the moving target based on the value of the at least one motion attribute of the reference and the previously established correlation; determining an end-point of the needle advancing path based on the value of the at least one motion attribute of the moving target; and advancing the biopsy needle at the determined time along the needle advancing path to allow a tip portion of the biopsy needle to reach the end-point of the needle advancing path.

Another exemplary aspect of the present disclosure relates to an image-guided needle biopsy system for performing needle biopsy on a moving target in a body. In one aspect, the disclosure contemplates an image-guided robotic needle biopsy system. The system includes a biopsy needle having a tip portion; an imaging unit configured to acquire a plurality of images of the moving target within a predetermined timeframe; a processing unit configured to generate a motion model of the moving target based on the plurality of images, to generate a needle advancing path for the biopsy needle based on the motion model of the moving target and to establish a correlation between at least one motion attribute of the moving target and at least one motion attribute of a reference; a tracking unit configured to acquire at least one image of the reference; and a needle manipulating unit for advancing the biopsy needle into the patient. The processing unit is further configured to determine a value of the at least one motion attribute of the reference based on the at least one image of the reference, to determine a time for advancing the biopsy needle based on the value of the at least one motion attribute of the reference, to determine a value of the at least one motion attribute of the moving target based on the value of the at least one motion attribute of the reference and the correlation; and to determine an end-point of the needle advancing path, based on the value of the at least one motion attribute of the moving target. The needle manipulating unit is configured to advance the biopsy needle at the determined time along the needle advancing path to allow the tip portion of the biopsy needle to reach the end-point of the needle advancing path.

These and other aspects and advantages of the current disclosure will become apparent from the following detailed description considered in conjunction with the accompanying drawings. It is to be understood, however, that the drawings are designed solely for purposes of illustration and not as a definition of the limits of the disclosure, for which reference should be made to the appended claims. Moreover, the drawings are not necessarily drawn to scale and, unless otherwise indicated, they are merely intended to conceptually illustrate the structures and procedures described herein.

DETAILED DESCRIPTION

Figure 1:
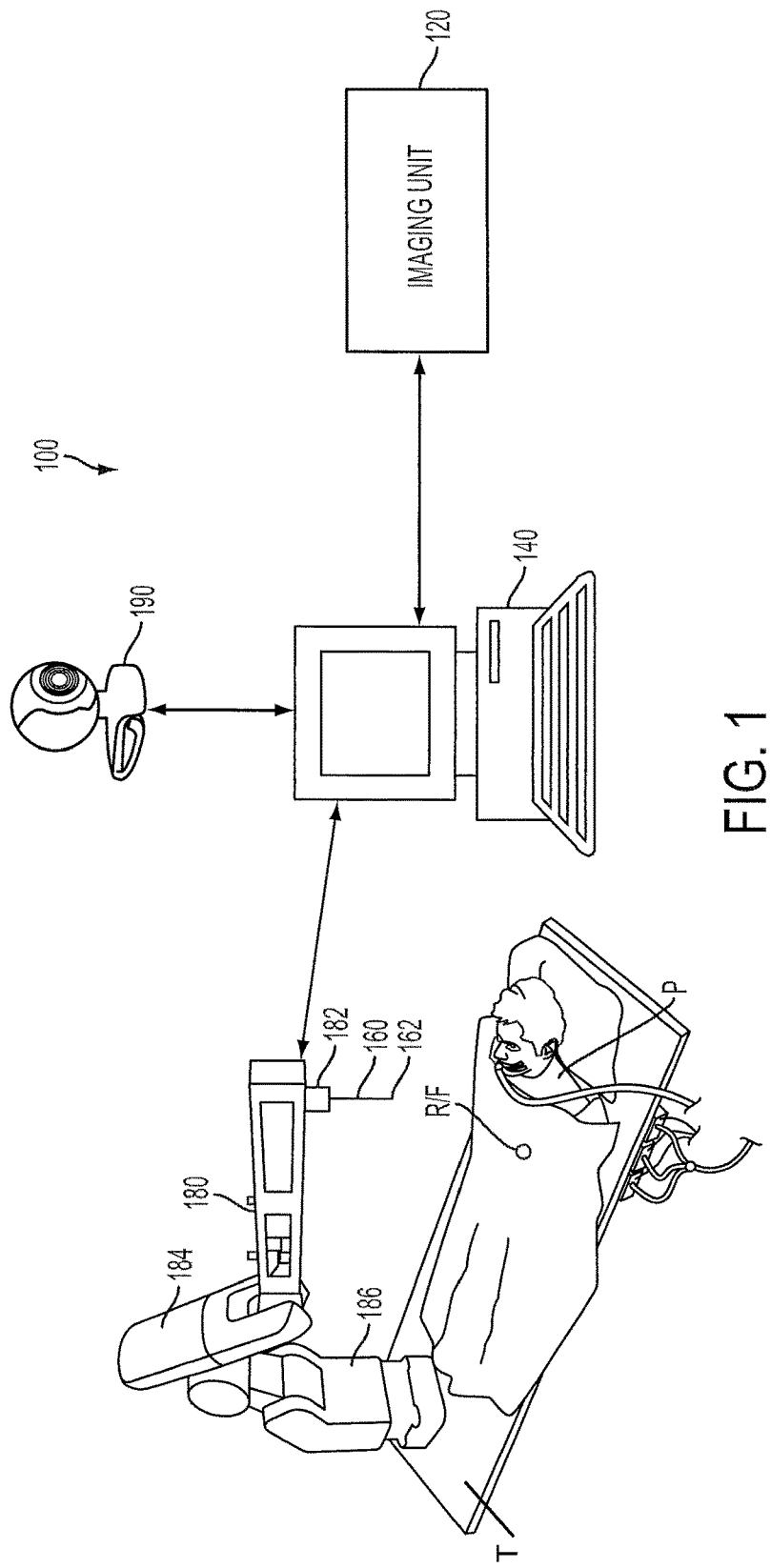
FIG. 1 is a block view of an image-guided needle biopsy system for performing needle biopsy on a moving target in a body, according to an exemplary aspect of the disclosure.

FIG. 1 is a block view of an image-guided needle biopsy system 100 for performing needle biopsy on a moving target in a biological body according to an exemplary aspect of the disclosure.

In general, the system 100 includes an imaging unit 120 configured to acquire a plurality of images of the moving target and a processing unit 140 in communication with the imaging unit 120 for processing image-related data and controlling the operation of the system. The processing unit 140 can be any suitable computer-related entity as long as it is capable of executing the functionalities thereof. For example, the processing unit 140 includes a central computer (PC) for controlling and coordinating the different units of the system 100.

The system 100 further includes a biopsy needle 160 having a tip portion 162 disposed at a distal end of the needle 160. The tip portion 162 is configured to penetrate bodily tissue of a patient P, particularly to sample a lung nodule of the patient P. Any suitable needles can be applied depending on, for example, the location of the nodule, the depth of the nodule and so on. For example, the needle 160 can be a coaxial needle set, which includes a stylet and a cannula.

During the biopsy procedure, the patient P lies on a stable operation table T. A skin-surface reference R is provided for the lung nodule of the patient P. The motion of the reference R is associated with the motion of the moving target and the correlation therebetween can be identified by the processing unit 140. Typically, the reference R is capable of moving concomitantly with the movement of the lung nodule and the motion state of the reference R can be captured and subsequently fed to the processing unit 140. For example, the reference R includes a CT-compatible fiducial marker F attached to the skin surface of the patient P, which can include a bright color marker for better distinction from a normal background in a regular visual camera image, or an infrared marker for easy tracking using an infrared camera.

The imaging unit 120 is configured to acquire a plurality of images of the lung nodule within a predetermined timeframe, for example, one or more respiratory cycles of the lung. Typically, a respiratory cycle of the lung takes 4 seconds. During the image acquiring process, the respiratory cycle is equally divided into 10 phases, which are labeled as 0, 10, 20, 30, 40, 50, 60, 70, 80 and 90, respectively.

The imaging unit 120 can include a CT unit for performing a series of pre-operative CT scans on the patient P under the free, relaxed breathing condition, from which a sequence of volumetric CT images corresponding to the patient P respiratory phases can be obtained. The 3D position of the lung nodule at each phase is obtained through the imaging unit 120. The imaging unit 120 can also be used to perform intra-operative and post-operative scans for other functions, such as confirming the biopsy result.

The acquired CT images can also show intervening structures/organs between the lung and the skin surface of the patient P, such as the rib cage, heart, major vessels, diaphragm and mediastinum.

High-contrast resolution of CT results in high imaging details of both hard and soft body tissues, in particular small lung nodules located deep within the lung or near blood vessels, airways or nerves. Thus, a CT imaging unit is found as a suitable implement for the imaging unit 120. However, whenever other imaging modalities are applicable, such as ultrasound machines and MR machines, they can be used without departing from the inventive concept of the present disclosure.

Relaxation medication can be administered to the patient P to relax and stabilize the respiration for reliable respiratory motion modeling and tracking.

The system further includes a needle manipulating unit 180, in communication with the processing unit 140, for controlling movement of the biopsy needle 160 to implement intended operations of the biopsy needle 160 upon receiving instructions from the processing unit 140. The needle manipulating unit 180 can be robotic. The manipulating unit 180 can be fixedly mounted to the table T or coordinated with the table T, through any suitable means. For example, the manipulating unit 180 can be a robotic manipulator including a gripper 182 configured to securely grip a proximal end of the needle 160 and an arm 184 for moving and rotating the needle 160. The manipulating unit 180 can optionally include a control unit 186 for controlling the motion of the components of the manipulator and communicating with the processing unit 140 to provide feedback information.

For example, a Mitsubishi® RV-E2 general-purpose 6-DOF articulated robot manipulator can be used for needle manipulation. The robot arm of this manipulator has six rotational joints and can position and move itself in both the joint space and a Cartesian coordinate system. The manipulator has a position repeatability of +/−0.04 mm and a positioning accuracy of 0.1 mm along X, Y and Z axes of the coordinate system. The maximal programmable linear speed of the end-effector is 650 mm/s. The robot has a dedicated controller the lower-level control and drive of the robot motion. The controller is connected to the central computer through an RS232 serial port. The robot control program can be edited on the computer and uploaded to the controller. For example, when programmed to advance the needle at 564.4 mm/second, it takes <0.285 seconds to advance the needle across an insertion distance of 150-160 mm, which is within one typical respiratory phase.

Although the robot controller can save a whole control program onboard and execute it on its own, it has very limited onboard computation ability and I/O ability to interface with other devices. Thus the robot controller has limited capability of managing the control flow. To enable adaptive feedback control of the robot, the central computer is configured to manage the control flow for the robot to allow the robot controller to work in a single-command mode. Accordingly, the central computer sends robot control commands, one after another, to the robot controller through the RS232 connection; the robot controller executes each command immediately upon receiving it. The capabilities that the central computer has to compute and interface allow satisfactory integration between the robot manipulator and other components and optional sensors, which leads to more flexible and robust feedback control of the robot.

Moreover, considering the patient safety, an emergency needle release function can be added. For example, a group of pressure sensors can be attached to the needle gripper 182 to monitor the force acting on the needle 160 in real time. If the needle 160 is under a significant force imbalance caused by the patient P (such as an abrupt movement of the patient or contact with the rib cage), the gripper 182 will release the needle 160 immediately to allow the needle 160 to be retracted. Subsequently, the biopsy procedure is aborted.

The needle gripper 182 can have its own control unit which interfaces with the robot controller 186. When the needle 160 is delivered to the target position, the robot controller 186 will send a signal (as the outcome of a robot control I/O command) to the gripper controller to trigger the needle release. Moreover, the above-mentioned emergency needle release function can be accomplished by constantly monitoring force feedback from the sensors and reactively triggering needle release by the gripper controller based on the detected force imbalance.

The system further includes a tracking unit 190 configured to track and monitor the motion state of the reference R by, for example, capturing images of the reference R. The tracking unit 190 is in communication with the processing unit 140 through a wireless or wired connection. For example, the tracking unit 190 can be connected to the processing unit 140 through a USB connection.

For example, a regular or infrared video camera can be used as the tracking unit 190 to track and monitor the fiducial marker F by transferring one or more RGB-color images to the processing unit 140. For example, a Logitech C250 webcam can be used, which has a resolution of 640×480 pixels and can capture 30 frames per second. The camera can be set up in a manner which allows the entire motion path of the marker F to fall into a field of view. While the CT unit performs pre-operative CT scanning to record the respiratory motion path of the target lung nodule, the camera acquires a plurality of images of the fiducial marker F to record the motion the fiducial marker. The camera can also acquire intra-operative images of the fiducial marker F to determine the current position of the marker.

Before an operation on a patient, the images acquired by the imaging unit 120, showing the lung nodule and other related organs and structures, are sent through wired or wireless connection to the processing unit 140, which can be any suitable computer-related entity as long as it is capable of executing the functionality thereof.

The processing unit 140 generates a motion model of the lung nodule by processing the images acquired by the imaging unit 120 over one or more respiratory cycles of the patient P. For example, the motion model can be any suitable graphical representation indicative of or associated with the motion of the nodule within a respiratory cycle of the patient P.

Figure 2A:
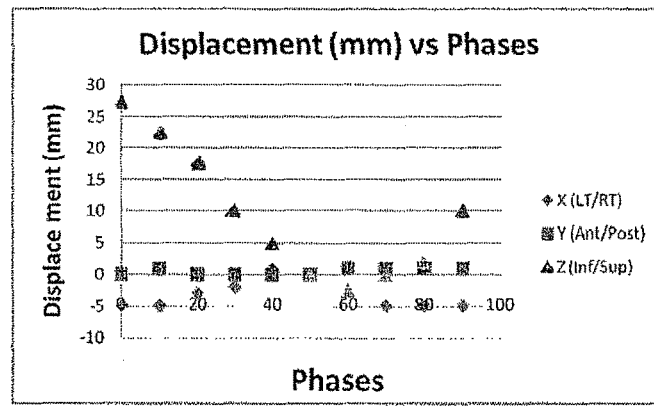
FIG. 2A-2C are representative diagrams of motion models of the moving target.
Figure 2B:
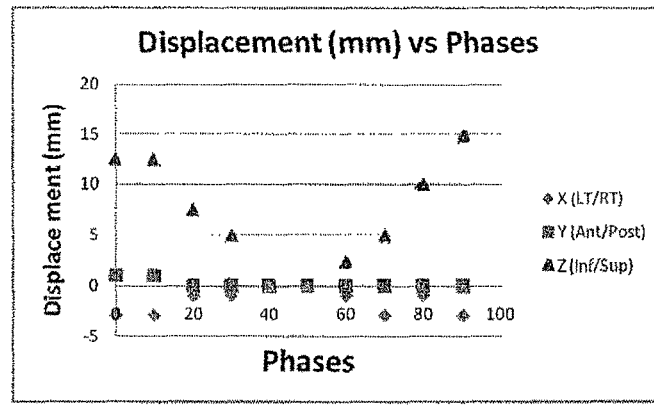
Figure 2C:
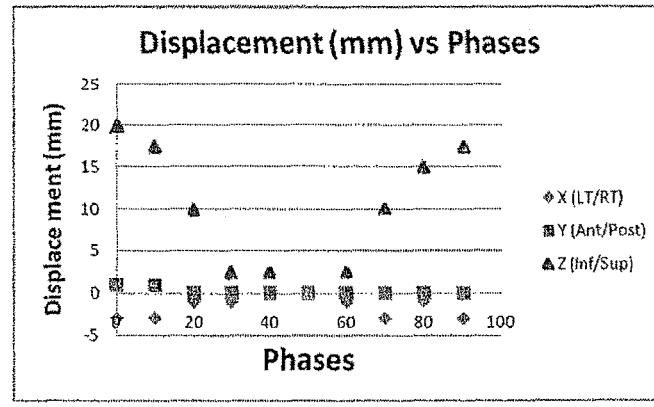

FIGS. 2A-2C illustrate three representative schematic diagrams, each of which illustrates a model in the form of a lung nodule motion path.

The processing unit 140 initially retrieves at least one set of nodule motion data from the images acquired by the imaging unit 120. For example, the processing unit 140 retrieves data relative to the X, Y and Z directions of a coordinate system predefined in the 4DCT system. Each set of data is processed to represent a periodic respiratory motion path of the lung nodule.

As previously described, 3D images of the lung nodule have been acquired at each phrase of a respiratory cycle. The data indicative of the motion of the lung nodule at each phase is retrieved by the processing unit 140, which reflects certain typical motion attributes including but not limited to the position of the lung nodule, the motion range of the lung nodule, the velocity of the lung nodule and the like. Typically, the range of the lung nodule motion ranges from 10 mm to 20 mm; the velocity of the lung nodule motion varies from phase to phase.

FIGS. 2A-2C illustrate the displacement of the lung nodule in the predefined three-dimensional coordinate system with respect to each phase of a respiratory cycle. As indicated in the figures, there are phrases in which the velocity of the nodule is close to zero (the value of the displacement of the lung nodule along each direction is close to zero), such as the phase 50 in each figure, which corresponds to a peak exhalation of the lung. Phases associated with low velocity are suitable time for advancing the needle.

Although the above exemplary description is made with respect to a lung nodule having a respiratory cycle, the inventive concept of the disclosure can be applied to any moving target with a human body, the motion of which optionally includes a periodic motion having a peak and trough. For example, when the motion is at the trough, the target's motion is of the lowest speed.

Based on the motion model of the lung nodule, such as the lung nodule respiratory motion paths shown in FIGS. 2A-2C, the processing unit 140 generates at least one suitable needle advancing path for the biopsy needle 160.

For example, based on the lung nodule respiratory motion paths shown in FIGS. 2A-2C, the processing unit 140 can generate a plurality of needle advancing paths from different directions relative to the nodule motion paths. Based on the respiratory motion model, an optimal straight-line needle path will be planned by comprehensively considering the needle travel distance under the skin, nodule motion state in each respiratory phase, and existence of interfering internal structures/organs. Correspondingly, a respiratory window will be chosen, consisting of one or more successive respiratory phases in which the lung nodule is at its lowest speed. The needle will be advanced within the chosen respiratory window, in order to minimize the chance of target missing and the control effort.

For example, a total of 150 different needle advancing paths can be generated. For example, with each lung nodule motion path, the needle advancing paths are uniformly chosen in a ±30 degree cone around the axis, which passes through the targeted needle-placement position on the lung nodule motion path and extends along a direction substantially perpendicular to an approximated plane of lung nodule motion.

The processing unit 140 further establishes a correlation between at least one motion attribute of the lung nodule and at least one motion attribute of the reference R, the motion of which can be tracked and monitored by the tracking unit 190.

For example, the correlation can be established by processing data retrieved from the images of the lung nodule acquired by the imaging unit 120 and data retrieved from the images of the reference R acquired by the tacking unit 190. Alternatively, the images acquired by the imaging unit 120, which shows both the lung nodule and the reference R, can be processed to establish the correlation.

The motion attribute includes but is not limited to the position, orientation, velocity, motion range and moving timing (such as a phase of the respiratory circle) of the lung nodule and the position, orientation, velocity, motion range and moving timing (such as a phase of the respiratory circle) of the reference R.

The processing unit 140 further processes the data from the images acquired by the tracking unit 190, such as a camera, to determine a value of at least one motion attribute of the reference R. For example, the value can be indicative of a position of the colored fiducial marker when the marker is moving along a motion path.

For example, each received image is processed to segment the marker from the image by using a filter based on a pixel intensity threshold. The output of the processing can be a binary logical image, wherein 1s represent the pixels in the region of the marker F as a bright spot and 0 s represent other pixels as a dark background. The position of the marker in the output image can be represented by the position of its top left corner. The moving direction of the marker is also retrieved based on the variation of its position in a sequence of output images.

It is within the scope of the present disclosure that the processing unit 140 can process the images from the tracking unit 190 to determine a value for each motion attribute of the reference R. All the determined values can be further processed to generate a composite indicator representative of the motion of the reference R. For example, the composite indicator can be representative of the current location of the reference R at a certain time and the moving velocity of the reference R along a certain direction.

The values of the motion attributes of the reference R are processed by the processing unit 140 to determine a time (e.g., the appropriate timing) for advancing the biopsy needle 160 along the predetermined needle advancing path. For example, the values can be processed to determine a respiratory phase of the targeted lung nodule (such as the peak exhalation when the velocity of the nodule is zero or close to zero), in which the biopsy needle is manipulated to approach the lung nodule. For example, during operation, the processing unit 140 processes each current image of the reference R to determine a value, and subsequently compares the value with a preset motion curve to determine the respiratory phase of the lung. This operation can be repeated until it is determined that the current respiratory phase is suitable for advancing the needle 160.

Based on the value of the at least one motion attribute of the reference R and correlation between the lung nodule and the reference R, the processing unit 140 further determines a value of at least one motion attribute of the lung nodule. Similarly, the value of the motion attribute of the lung nodule is indicative of a motion state including but not limited to the position, orientation, velocity, motion range and respiratory phase of the lung nodule. The value of the motion attribute of the lung nodule can be further processed by the processing unit 140 to determine an end-point of the needle advancing path.

Based on the determined optimal needle advancing path, the time suitable for advancing the needle and the end-point of the needle advancing path, the processing unit 140 generates an instruction signal and sends the signal to the manipulating unit 180.

Upon receiving the instruction signal, the manipulating unit 180 controls the operation of the arm 184 and the gripper 182 to drive the needle 160 along the needle advancing path at the predetermined time to allow the tip portion 162 of the needle 160 to safely and efficiently reach the end-point of the needle advancing path. Accordingly, the needle placement is accomplished. A local anesthesia can be optionally injected to numb the path of the needle in order to minimize the patient's reaction to the needle insertion.

Figure 3:
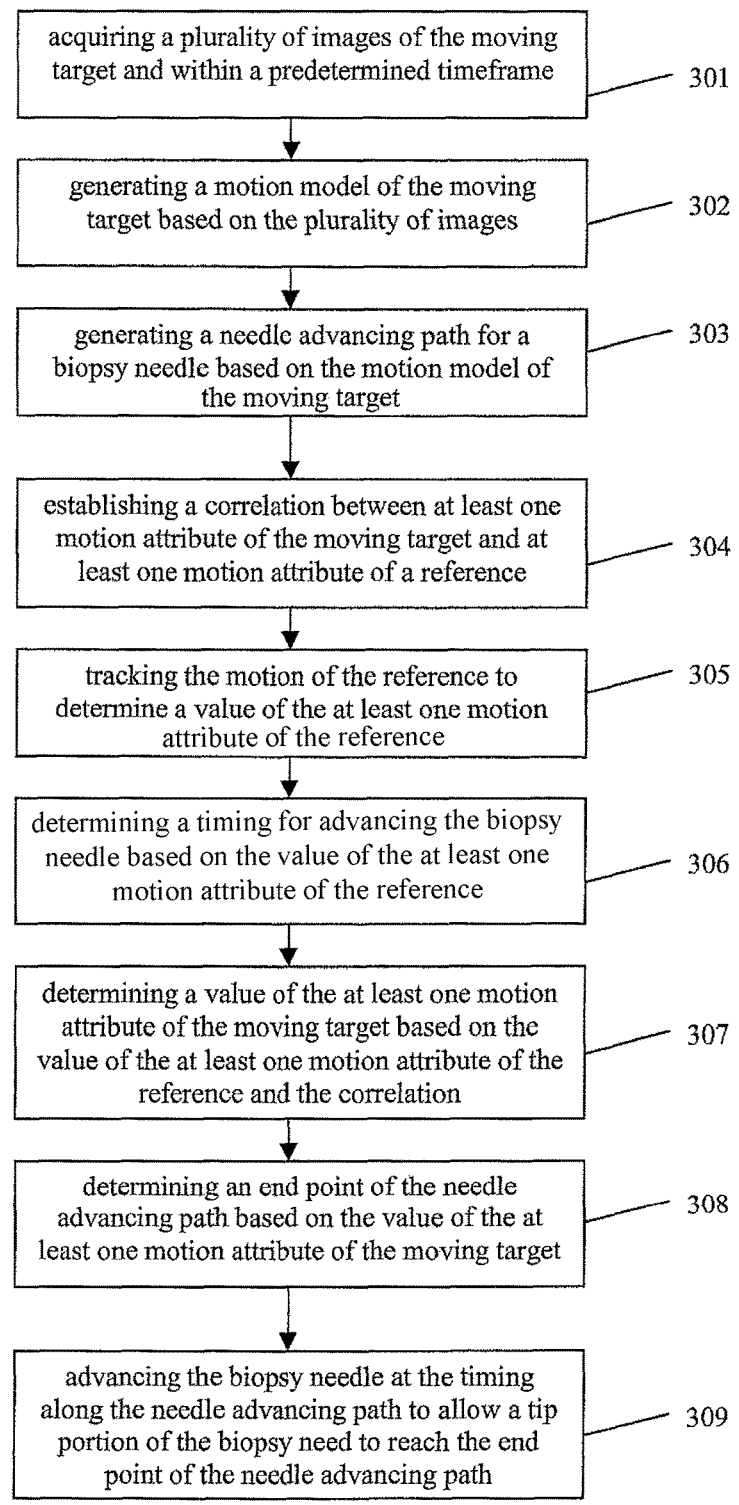
FIG. 3 is a flow chart illustrating steps of a method of performing needle biopsy on a moving target in a body, according to another exemplary aspect of the disclosure.

FIG. 3 is a flow chart illustrating a method for performing needle biopsy on a moving target in a body, according to another exemplary aspect of the disclosure.

At step 301, a plurality of images of the moving target are acquired during a predetermined timeframe. In this step, the images can be acquired through CT scanning.

At step 302, a motion model of the moving target is generated based on the plurality of images. The motion of the moving target can be a periodic motion having a peak and a trough.

At step 303, a needle advancing path for a biopsy needle is generated based on the motion model of the moving target. In this step, motions of at least one intervening object between the moving target and a surface of the body, a distance between the moving target and a surface of the body and/or an angle between the needle and a surface of the body can be considered in generating the needle advancing path. In this step, a straight needle advancing path can be generated.

At step 304, a correlation between at least one motion attribute of the moving target and at least one motion attribute of a reference is established. In this step, the reference can be on a surface of the body. The attribute includes at least one of a position, an orientation, a velocity, a motion range and a timing sequence or a time determination.

At step 305, the motion of the reference is tracked to determine a value of the at least one motion attribute of the reference. For example, the value can be determined based on an acquired image of the reference. This step can further include attaching a fiducial marker to the reference and tracking the motion of the marker through video.

At step 306, the time for advancing the biopsy needle is determined based on the value of the at least one motion attribute of the moving target. This step includes determining a time when the periodic motion of the moving target is at its trough.

At step 307, a value of the at least one motion attribute of the moving target is determined based on the value of the at least one motion attribute of the reference and the correlation. At step 308, an end-point of the needle advancing path is determined based on the value of the at least one motion attribute of the moving target.

At step 309, the biopsy needle is advanced at the determined time along the needle advancing path to allow a tip of the needle to reach the end-point. This step can include generating an instruction signal based on the predetermined time, needle advancing path and end-point of the path and sending the instruction signal to a needle manipulating unit to drive the needle at the time along the needle advancing path to allow a tip of the needle to reach the end-point of the path.

The method can further include releasing the biopsy needle based on feedback of at least one sensor, which can be attached to a gripper of the manipulating unit. The above steps can be controlled and coordinated by a central computer.

The CT-guided robotic needle biopsy system and method, as described and shown in the previous exemplary embodiments of the present disclosure, improve biopsy accuracy and reduce biopsy duration for performing a lung nodule biopsy. The system and method do not require the patients to hold their breath. Accordingly, patient comfort and safety can be improved and human intervention can be minimized.

In addition, the procedure duration of the conventional biopsy technology ranges from 15 minutes to over an hour, depending on CT, cytology availability, nodule accessibility and patient compliance. In contrast, according to the biopsy system and method of the disclosure, the procedure duration can be significantly reduced to range from several minutes to one minute or less.

While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

What is claimed is:

1. A method of performing needle biopsy on a moving target in a body, the method comprising:
    acquiring a plurality of images of the moving target within a predetermined timeframe;
    generating a motion model of the moving target based on the plurality of images;
    generating a needle advancing path for a biopsy needle based on the motion model of the moving target;
    establishing a correlation between at least one motion attribute of the moving target and at least one motion attribute of a reference;
    tracking the motion of the reference to determine a value of the at least one motion attribute of the reference;
    determining a time for advancing the biopsy needle based on the value of the at least one motion attribute of the reference;
    determining a value of the at least one motion attribute of the moving target based on the value of the at least one motion attribute of the reference and the established correlation;
    determining an end-point of the needle advancing path based on the value of the at least one motion attribute of the moving target; and
    advancing the biopsy needle at the determined time along the needle advancing path to allow a tip portion of the biopsy needle to reach the end-point of the needle advancing path.

2. The method of claim 1, further comprising releasing the biopsy needle based on feedback of at least one sensor.

3. The method of claim 1, wherein said reference comprises a fiducial marker attached to a surface of the body and said tracking the motion of the reference comprises tracking the fiducial marker through video.

4. The method of claim 1, wherein said generating a needle advancing path comprises generating a needle advancing path for the biopsy needle based on the motion model of the moving target and motions of at least one intervening object between the moving target and a surface of the body.

5. The method of claim 1, wherein said generating a needle advancing path comprises generating a needle advancing path for the biopsy needle based on the motion model of the moving target and a distance between the moving target and a surface of the body.

6. The method of claim 1, wherein said generating a needle advancing path comprises generating a needle advancing path for the biopsy needle based on the motion model of the moving target and an angle between the needle and a surface of the body.

7. The method of claim 1, wherein said generating a needle advancing path comprises generating a straight needle advancing path for the biopsy needle based on the motion model.

8. The method of claim 1, wherein said acquiring a plurality of images of the moving target within a predetermined timeframe comprises acquiring a plurality of CT images of the moving target within a predetermined timeframe.

9. The method of claim 1, wherein the at least one motion attribute of the moving target comprises at least one of a position, an orientation, a velocity, a motion range and a timing of the moving target and the at least one motion attribute of the reference comprises at least one of a position, an orientation, a velocity, a motion range and a timing of the reference.

10. The method of claim 1, wherein the motion of the moving target comprises a periodic motion having a peak and a trough and said determining a time for advancing the biopsy needle comprises determining a time based on the value of the at least one motion attribute of the moving target, when the periodic motion of the moving target is at the trough thereof.

11. An image-guided needle biopsy system for performing needle biopsy on a moving target in a body, the system comprising:
a biopsy needle having a tip portion;
an imager selected from the group consisting of a CT imager, an ultrasonic imager and an MR imager, the imager configured to acquire a plurality of images of the moving target within a predetermined timeframe;
a processor configured to generate a motion model of the moving target based on the plurality of images, generate a needle advancing path for the biopsy needle based on the motion model of the moving target and establish a correlation between at least one motion attribute of the moving target and at least one motion attribute of a reference;
a camera configured to acquire at least one image of the reference; and
a robotic needle manipulator for advancing the biopsy needle into the body,
wherein the processor is further configured to:
determine a value of the at least one motion attribute of the reference based on the at least one image of the reference;
determine a time for advancing the biopsy needle based on the value of the at least one motion attribute of the reference;
determine a value of the at least one motion attribute of the moving target based on the value of the at least one motion attribute of the reference and the correlation; and
determine an end-point of the needle advancing path based on the value of the at least one motion attribute of the moving target, and
wherein the robotic needle manipulator is configured to advance the biopsy needle at the determined time along the needle advancing path to allow the tip portion of the biopsy needle to reach the end-point of the needle advancing path.

12. The system of claim 11, wherein the reference comprises a fiducial marker configured to attach to a surface of the body and the camera is configured to acquire at least one video image of the fiducial marker.

13. The system of claim 11, wherein said processor is further configured to generate a needle advancing path based on the motion model of the moving target and motions of at least one intervening object between the moving target and a surface of the body.

14. The system of claim 11, wherein said processor is further configured to generate a needle advancing path for the biopsy needle based on the motion model of the moving target and a distance between the moving target and a surface of the body.

15. The system of claim 11, wherein said processor is further configured to generate a needle advancing path for the biopsy needle based on the motion model of the moving target and an angle between the needle and a surface of the body.

16. The system of claim 11, wherein the at least one motion attribute of the moving target comprises at least one of a position, an orientation, a velocity, a motion range and a timing of the moving target and the at least one motion attribute of the reference comprises at least one of a position, an orientation, a velocity, a motion range and a timing of the reference.

17. The system of claim 11, wherein the motion of moving target comprises a periodic motion having a peak and a trough and said processor is further configured to determine a time for advancing the biopsy needle when the periodic motion of the moving target is at the trough thereof.

18. A non-transitory computer readable storage medium storing a program of instructions executable by a machine to perform a method for performing biopsy on a moving target, said method comprising:
acquiring a plurality of images of the moving target within a predetermined timeframe;
generating a motion model of the moving target based on the plurality of images;
generating a needle advancing path for a biopsy needle based on the motion model of the moving target;
establishing a correlation between at least one motion attribute of the moving target and at least one motion attribute of a reference;
tracking the motion of the reference to determine a value of the at least one motion attribute of the reference;
determining a time for advancing the biopsy needle based on the value of the at least one motion attribute of the reference;
determining a value of the at least one motion attribute of the moving target based on the value of the at least one motion attribute of the reference and the correlation;
determining an end-point of the needle advancing path based on the value of the at least one motion attribute of the moving target; and
advancing the biopsy needle at the determined time along the needle advancing path to allow a tip portion of the biopsy needle to reach the end-point of the needle advancing path.

* * * * *